United States Patent
Sharif et al.

(10) Patent No.: US 6,492,417 B1
(45) Date of Patent: Dec. 10, 2002

(54) 11-DEOXY-16-FLUORO-PGF$_{2\alpha}$ ANALOGS AS FP RECEPTOR ANTAGONISTS

(75) Inventors: Najam A. Sharif, Arlington, TX (US); Brenda W. Griffin, Colleyville, TX (US)

(73) Assignee: Alcon Manufacturing, Ltd., Forth Worth, TX (US)

( * ) Notice: Subject to any disclaimer, the term of this patent is extended or adjusted under 35 U.S.C. 154(b) by 0 days.

(21) Appl. No.: 09/211,599

(22) Filed: Dec. 14, 1998

Related U.S. Application Data

(60) Provisional application No. 60/068,469, filed on Dec. 22, 1997.

(51) Int. Cl.$^7$ .............................................. A62K 31/215
(52) U.S. Cl. ........................ 514/530; 514/573; 514/912
(58) Field of Search ................................ 514/530, 573, 514/912

(56) References Cited

U.S. PATENT DOCUMENTS

| | | | |
|---|---|---|---|
| 4,321,275 A | 3/1982 | Bowler | |
| 4,870,104 A | 9/1989 | Vorbruggen et al. | |

FOREIGN PATENT DOCUMENTS

| | | |
|---|---|---|
| EP | 364417 B1 | 4/1990 |
| WO | WO 94/06432 | 3/1994 |

OTHER PUBLICATIONS

Berridge, Inositol trisphosphate and calcium signalling *Nature* 361:315–325 (Jan. 1993).

Coleman et al., Prostanoids and their receptors, in *Comprehensive Medicinal Chemistry: The Rational Design, Mechanistic Study and Therapeutic Application of Chemical Compounds* (Hansch,C., Sammes, P.G., Taylor, J.B., Eds.) (Pergamon Press: New York, (Oxford)) 3:643–714 (1990).

Coleman et al., VIII International Union of Pharmacology classification of prostanoid receptors: Properties, Distribution, and structure of the receptors and their subtypes, *Pharmacol. Rev.*, 46:205–229 (1994).

Davis et al., Prostaglandin F$_{2\alpha}$ stimulates phosphatidylinositol 4,5–bisphosphate hydrolysis and mobilizes intracellular Ca$^{2+}$ in bovine luteal cells, *Proc. Natl. Acad. Sci.*, (USA) 84:3728–3732 (Jun. 1987).

Delaey and Van de Voorde, Prostanoid–induced contractions are blocked by sulfonylureas, *Eur. J. Pharmacol.*, 280:179–184 (1995).

Fitzpatrick et al., Antagonism of the pulmonary vasoconstrictor response to propstaglandin F$_{2\alpha}$ by N–dimethylamino Substitution of prostaglandin F$_{2\alpha}$, *J. Pharmacol. Exp. Ther.*, 206(1):139–142 (1978).

Griffin et al., FP prostaglandin receptors mediating inositol phosphates generation and calcium mobilization in Swiss 3T3 Cells: A pharmacological study, *J. Pharmacol. Exp. Ther.*, 281(2): 845–854 (1997).

Kitanaka et al., Phloretin as an antagonist of prostaglandin F$_{2\alpha}$ receptor in cultured rat astrocytes, *J. Neurochem.*, 60(2):704–708 (1993).

Maddox et al., Amide and I–amino derivatives of F prostaglandins as prostaglandin antagonists, *Nature*, 273: 549–552 (Jun. 1978).

Nakao et al., Characterization of prostaglandin F$_{2\alpha}$ receptor of mouse 3T3 fibroblasts and its functional expression in *Xenopus laevis* oocytes, *J. Cell. Physiol.*, 155: 257–264 (1993).

*Primary Examiner*—Zohreh Fay
(74) *Attorney, Agent, or Firm*—Barry L. Copeland

(57) ABSTRACT

Methods and compositions for the antagonism of FP receptor-mediated biological responses are disclosed.

9 Claims, 4 Drawing Sheets

Schild Analysis for Compound II as an FP Receptor Antagonist (in Swiss 3T3 and A7r5 Cells)

11-DEOXY-16-FLUORO-PGF$_{2\alpha}$ ANALOGS AS FP RECEPTOR ANTAGONISTS

This application claims the benefit of No. 60/068,469, filed Dec. 22, 1997.

FIELD OF THE INVENTION

The present invention relates to the use of certain 11-deoxy-16-fluoro-PGF$_{2\alpha}$ analogs as FP receptor antagonists.

BACKGROUND OF THE INVENTION

The FP prostaglandin receptor belongs to a family of prostaglandin receptors, all of which have seven-transmembrane domains and couple to specific G-proteins. When activated by the binding of a specific ligand (a prostaglandin belonging to one of several defined classes of prostaglandins) the G-proteins transmit and amplify within the cell a signal to their preferred prostaglandin receptors on the surface of the cell membrane. (Coleman et al., VIII International Union of Pharmacology classification of prostanoid receptors: Properties, distribution, and structure of the receptors and their subtypes, *Pharmacol. Rev.*, 45:205–229 (1994)). Ligand-induced activation of the FP prostaglandin receptor is believed to involve activation of the enzyme phospholipase C (mediated by specific G-proteins), resulting in rapid hydrolysis of phosphatidylinositol 4,5-bisphosphate in the cell membrane. The products of this hydrolysis are inositol 1,4,5-triphosphate (IP$_3$) and diacylglycerol (DAG), which act as second messengers inside the cell. (Coleman et al., VIII International Union of Pharmacology classification of prostanoid receptors: Properties, distribution, and structure of the receptors and their subtypes, *Pharmacol. Rev.*, 46:205–229 (1994); Berridge, Inositol trisphosphate and calcium signaling, *Nature* 361:315–325 (1993); Davis et al., Prostaglandin F$_{2\alpha}$ stimulates phosphatidylinositol 4,5-bisphosphate hydrolysis and mobilizes intracellular Ca$^{2+}$ in bovine luteal cells, *Proc. Natl. Acad. Sci.*, (USA) 84:3728–3732 (1987); Nakao et al., Characterization of prostaglandin F$_{2\alpha}$ receptor of mouse 3T3fibroblasts and its functional expression in *Xenopus laevis* oocytes, *J. Cell. Physiol.* 155: 257–264 (1993); and Griffin et al., FP prostaglandin receptors mediating inositol phosphates generation and calcium mobilization in Swiss 3T3 Cells: A pharmacological study, *J. Pharmacol. Exp. Ther.* 281: 845–854 (1997)). IP$_3$ mobilizes Ca$^{2+}$ from intracellular stores and DAG activates protein kinase C. Together these second messengers activate various enzymes and other proteins to produce the final biological responses. The latter may involve tissue contraction, hormone release, fluid secretion, or initiation of an inflammatory response.

Like most prostaglandin receptors, the FP prostaglandin receptor is broadly distributed in human and animal tissues. Various endogenous prostaglandins, arising from the action of cyclooxygenases on arachidonic acid, can bind to and activate the FP receptor, with prostaglandin F$_{2\alpha}$ (PGF$_{2\alpha}$) being the most potent FP agonist of these endogenous ligands. Therapeutic applications of FP receptor activation using such endogenous prostaglandins are known. (Coleman et al., Prostanoids and their receptors, in *Comprehensive Medicinal Chemistry: The Rational Design, Mechanistic Study and Therapeutic Application of Chemical Compounds* (Hansch,C., Sammes, P. G., Taylor, J. B., Eds.) (Pergamon Press: New York, (Oxford)) 3:674 (1990); and Coleman et al., VIII International Union of Pharmacology classification of prostanoid receptors: Properties, distribution, and structure of the receptors and their subtypes, *Pharmacol. Rev.*, 45:205–229 (1994)).

Characterization of the functions of the various prostaglandin receptors has been advanced by the availability of synthetic analogs of the endogenous prostaglandins. Many such analogs have been prepared and described in the literature. (Coleman et al., Prostanoids and their receptors, in *Comprehensive Medicinal Chemistry: The Rational Design, Mechanistic Study and Therapeutic Application of Chemical Compounds* (Hansch,C., Sammes, P. G., Taylor, J. B., Eds.) (Pergamon Press: New York, (Oxford)) 3:674 (1990).

In general, rational design of structural analogs of the endogenous prostaglandins based on empirically-derived structure-activity relationships has resulted in more potent and more selective agonists at the various prostaglandin receptors. The availability of well-characterized potent and selective agonists at the FP and other prostaglandin receptors has increased understanding of the in vivo pharmacological (and potential therapeutic) actions of both the specific prostaglandin analogs and the specific prostaglandin receptors to which they bind. However, it has now been discovered that potent and selective receptor antagonists serve a complementary function in defining the physiologic and pharmacological roles of receptors, and in certain instances are themselves valuable therapeutic agents.

There are only a few classes of prostaglandin receptors for which antagonists with defined chemical structures and well-characterized antagonistic biological activities have been identified. (Coleman et al., VIII International Union of Pharmacology classification of prostanoid receptors: Properties, distribution, and structure of the receptors and their subtypes, *Pharmacol. Rev.*, 45:205–229 (1994)). For the FP receptor, compounds suggested to be or classified as antagonists include the dimethylamide and dimethylamine of PGF$_{2\alpha}$ (Maddox et al., Amide and I-amino derivatives of F prostaglandins as prostaglandin antagonists, *Nature*, 273: 549–552 (1978); (Fitzpatrick et al., Antagonism of the pulmonary vasoconstrictor response to prostaglandin F$_{2\alpha}$ by N-dimethylamino substitution ofprostaglandin F$_{2\alpha}$, *J. Pharmacol. Exp. Ther.*, 206:139–142 (1978)), phloretin (Kitanaka et al., Phloretin as an antagonist of prostaglandin F$_{2\alpha}$ receptor in cultured rat astrocytes, *J. Neurochem.*, 60:704–708 (1993)), glybenclamide and tolbutamide (Delaey and Van de Voorde, Prostanoid-induced contractions are blocked by sulfonylureas, *Eur. J. Pharmacol.*, 280:179–184 (1995)). Most of these compounds, however, are either inactive or very weak FP prostaglandin receptor antagonists with little or no selectivity at the FP prostaglandin receptor.

There remains a need, therefore, for potent and selective antagonists of the FP prostaglandin receptor that can be used for the general purposes of: 1) defining more precisely the function(s) of the FP prostaglandin receptor and its selective agonists in vivo and in vitro (e.g., as valuable pharmacological tools); 2) serving as a diagnostic tool for FP prostaglandin receptor function in various disease processes; 3) treating various conditions, diseases or untoward effects associated with FP receptor activation, such as ocular hyperemia, cystoid macular edema, iris hyperpigmentation or melanogenesis, excessive bone deposition, and premature labor.

SUMMARY OF THE INVENTION

The present invention is directed to the use of certain 11-deoxy-16-fluoro-PGF$_{2\alpha}$ analogs to antagonize FP receptor-mediated biological responses.

DETAILED DESCRIPTION OF THE INVENTION

Figure 1:
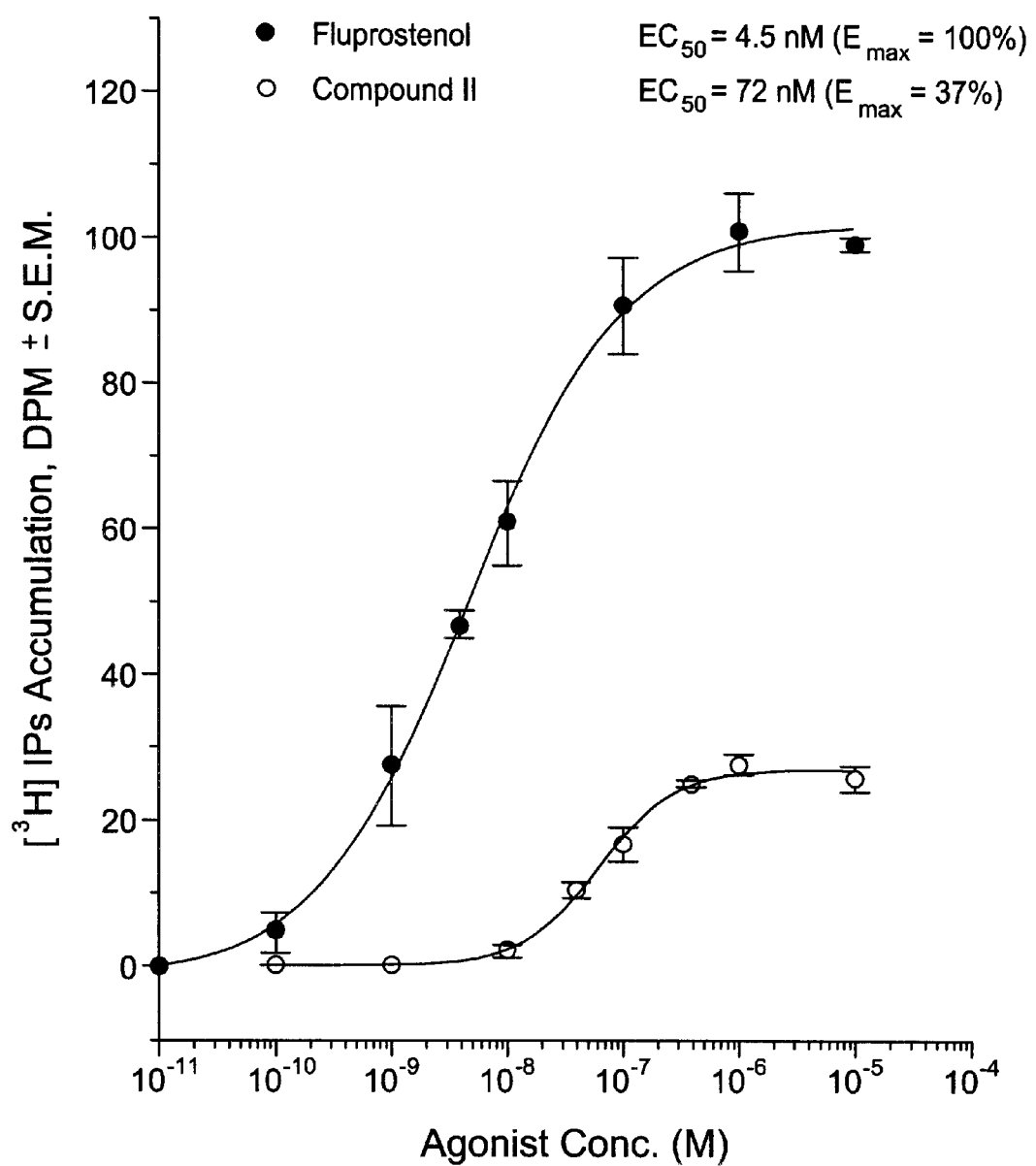
FIG. 1 is a graphical depiction of the concentration-dependent stimulation of the FP receptor by a standard FP agonist, fluprostenol, and Compound II on A7r5 cells and the consequential production of [$^3$H]IPs quantified by ion exchange chromatography.

It has unexpectedly been found that the 11-deoxy-16-fluoro-PGF$_{2\alpha}$ analogs of the present invention act as potent FP receptor antagonists, having utility as pharmacologic and diagnostic tools as well as true therapeutics. Specifically, the FP receptor antagonists of the present invention may be used for the general purposes of: 1) defining more precisely the function(s) of the FP prostaglandin receptor and its selective agonists in vivo and in vitro (e.g., as valuable pharmacological tools); 2) serving as a diagnostic tool for FP prostaglandin receptor function in various disease processes; 3) treating various conditions, diseases or untoward effects associated with FP receptor activation, such as ocular hyperemia, cystoid macular edema, iris hyperpigmentation or melanogenesis, excessive bone deposition, and premature labor.

The substituted PGF$_{2\alpha}$ analogs useful in the methods and compositions of the present invention have the following formula I:

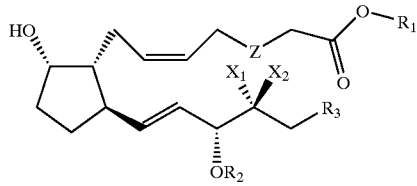

wherein:
R$_1$=H, C1–C5 alkyl or C3–C6 cycloalkyl, or a cationic salt moiety;
Z=(CH$_2$)$_n$, O, NH, or S; where n=1–3;
R$_2$=H, C1–C5 alkyl, or acyl;
one of X$_1$ or X$_2$=H, and the other halo; or X$_1$=X$_2$=halo; and
R$_3$=(CH$_2$)$_2$CH$_3$ or phenyl; where the phenyl is optionally substituted with halogen, CH$_3$, CF$_3$, CN, OCH$_3$ or acetyl.

Preferred compounds for use in this invention are of the formula II:

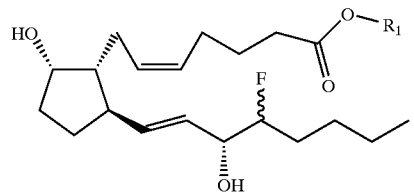

wherein:
R$_1$=H or isopropyl.

Especially preferred for use in the methods and compositions of the present invention are those compounds of formula II above, wherein R$_1$=H, i.e. a carboxylic acid form of the compound, which will be referred to herein as Compound II.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cylopentyl and cyclohexyl.

The term "alkenyl" includes straight or branched chain hydrocarbon groups having 1 to 15 carbon atoms with at least one carbon-carbon double bond. The chain hydrogens may be substituted with other groups, such as halogen. Preferred straight or branched alkeny groups include, allyl, 1-butenyl, 1-methyl-2-propenyl and 4-pentenyl.

The term "alkynyl" includes straight or branched chain hydrocarbon groups having 1 to 15 carbon atoms with at least one carbon-carbon triple bond. The chain hydrogens may be substituted with other groups, such as halogen. Preferred straight or branched alkynyl groups include, 2-propynyl, 2-butynyl, 3-butynyl, 1-methyl-2-propynyl and 2-pentynyl.

The term "alkoxy" represents an alkyl group attached through an oxygen linkage.

The term "alkylamino" represents an alkyl group attached through a nitrogen linkage.

The term "dialkylamino" represents two alkyl groups attached through a nitrogen linkage.

The term "lower alkyl" represents alkyl groups containing one to six carbons (C1–C6).

The term "halogen" represents fluoro, chloro, bromo, or iodo.

The term "aryl" refers to carbon-based rings which are aromatic. Aromatic rings have alternating double and single bonds between an even number of atoms forming a system which is said to 'resonate'. The rings may be isolated, such as phenyl, or fused, such as naphthyl. The ring hydrogens may be substituted with other groups, such as lower alkyl, or halogen.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include. imidazole, pyridine, indole, quinoline, furan, thiophene, pyrrole, tetrahydroquinoline, dihydrobenzofuran, and dihydrobenzindole.

In the foregoing illustrations, as well as those provided hereinafter, wavy line attachments indicate either the alpha (α) or beta (β) configuration. A hatched line, as use e.g. at carbon 9, indicates the α configuration. A solid triangular line indicates the β configuration.

Other related PGFs within the scope of the present invention are known and their syntheses are either described in the literature or can be achieved by methods similar to those described in the literature or otherwise known to those of skill in the art. See, for example, U.S. Pat. Nos. 4,321,275 and 4,870,104, and EP 364417 B1. The foregoing references are by this reference incorporated herein.

FP prostaglandin receptors are found in many organs of the body and have been implicated in many disorders/diseases. In addition, it is now believed that some of the side-effects of FP prostaglandins when topically applied to treat glaucoma, such as ocular surface hyperemia, iris hyperpigmentation and cystoid macular edema in the retina, may result from activation of the FP receptor. The FP receptor antagonists of the present invention are therefore useful as therapeutic agents to combat the afore-mentioned side-effects. Other therapeutic uses of the FP antagonists of this invention would include without limitation: treatment of acute and/or chronic inflammatory conditions, preventing excessive bone deposition, treating benign prostatic hypertrophy, treating uterine cramps, irritable bowel disease, cardiac arrythmias, epilepsy or conditions resulting from the same, prevention or ameliorating of certain degenerative diseases, and improving function of the immune system. Moreover, the FP receptor antagonists of the present invention may be used as diagnostic and/or pharmacological tools to demonstrate the mechanism of action of prostaglandins working through the FP receptor in vitro and/or in vivo. An example of how such an agent would be used in vitro is described below and also demonstrated in FIGS. 2–4.

Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis* by J. D. Morrison and J. W. Scott, Ed., Academic Press Publishers: New York, 1983–1985 (five volumes published over a three year span with chapters contributed by about two dozen authors) and *Principles of Asymmetric Synthesis* by R. E. Gawley and J. Aube, Ed., Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*, G. Subramanian, Ed., VCH Publishers: New York, 1994; *Chiral Separations by HPLC*, A. M. Krstulovic, Ed., Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution or even mixing samples having different enantiomeric ratios. Also included within the scope of the invention are the individual isomers substantially free of their enantiomers.

The FP antagonists of the present invention may be conventionally formulated in the appropriate vehicle (e.g. water, gel, compressed tablet, etc. in the presence or absence of exipients as needed) suitable for topical ocular, oral, subcutaneous, intravenous or other routes of administration at the appropriate dose (e.g. 0.00003 to 1.0% for topical ocular use) determined by the physician/investigator skilled in the art. Depending on the purpose for which the compounds of this invention are used (e.g. for in vivo or in vitro antagonism of the FP receptor) and the method of their delivery, they may be used in one or more preferred chemical forms, for example, the ester and/or acylated alcohol pro-drugs of the core structures.

EXAMPLE 1

Measuring in vitro Pharmacological Activity of FP Receptor Agonists and Antagonists Confluent monolayer cultures of cells (in a standard 24-well tissue culture plate) expressing the FP receptor are exposed to [$^3$H]-myo-inositol (1.5 $\mu$Ci in a volume of 0.5 ml DMEM culture medium supplemented with 2 mM L-glutamine and 10 $\mu$g/ml gentamicin sulfate) in the absence of serum, which causes net incorporation of the radioisotope into the phosphotidylinositol membrane lipids. After 24–32 hrs, the medium with the radioisotope is removed and the cells are rinsed once with DMEM/F-12 medium containing 10 mM LiCl (assay medium). Then 0.5 ml of assay medium is added to each well of cells, followed by addition of varying concentrations of an FP receptor agonist (or other test compound). Cells are exposed to the test agent for 30–120 min in a humidified incubator (95% air/5% $CO_2$), maintained at 37° C. Then the assay medium is removed and 1 ml of 0.1 M formic acid is added to the cell monolayer to inactivate the phospholipase C and to the radiolabelled products into the assay medium. The presence of LiCl during the agonist stimulation period inhibits phosphatases and permits the accumulation of radiolabelled inositol phosphates (IPs) which is measured by ion exchange chromatography.

The agonist-dependent production of IPs, which reflects the degree of receptor activation, is quantitatively measured for each well of cells in the 24-well plate by separating the negatively charged radiolabelled IPs from other minor radiolabelled species and free [$^3$H]-myo-inositol by anion exchange chromatography. This is accomplished by adding 0.9 ml of the cell lysate obtained as described above to a column packed with 1 ml of AG 1-X8 anion exchange resin in the formate form. The elution and separation of the radiolabelled IPs from the column consists of sequential additions to the column of: 1) 10 ml of water; 2) 8 ml of 50 mM ammonium formate; and 3) 4 ml of 1.2 M ammonium formate solution containing 0.1 M formic acid. The first two washes are discarded, and the third is collected in a scintillation vial, to which is added 15 ml of a water-accepting scintillation fluid. These samples, i.e., the radiolabelled IPs formed by the cells in response to stimulation by an FP prostaglandin receptor agonist or other test agent, is then measured by scintillation spectrometry on a beta-counter.

The dependence of the level of the [$^3$H]IPs production on agonist concentration is analyzed by standard pharmacological methods to determine the potency ($EC_{50}$ value) and efficacy (maximum response; $E_{max}$) of the FP receptor agonist relative to a standard FP receptor agonist such as fluprostenol. The partial agonist activity of Compound II at the FP receptor is shown in FIG. 1. Compound II is classified as a partial agonist because the maximum effect of this compound is substantially lower than that of the reference (full agonist) compounds, fluprostenol (FIG. 1). For the evaluation of putative antagonists of the formation of IPs, cells are pre-incubated for 10–20 min with the putative antagonist (in this case Compound II) prior to adding the agonist, typically one of the more potent and selective FP agonists like cloprostenol or fluprostenol. The agonist stimulation is then continued for the standard time (30–120 min), after which the procedure for quenching the reaction, separating the [$^3$H]IPs, and anion exchange chromatography is identical to the procedure described above. A compound is considered to be an antagonist in this protocol if it inhibits the agonist-stimulated [$^3$H]IPs production relative to the production measured in the control experiment (performed in parallel), in which the solvent is substituted for the antagonist.

Two different antagonist protocols are employed: 1) the antagonist concentration is varied while holding the agonist concentration fixed at a concentration approximately 10 times the agonist $EC_{50}$ value and 2) the antagonist concentration is fixed in a given experiment, with the agonist concentration varied, and several such experiments, each with a different, fixed antagonist concentration, are performed. The first protocol yields an inhibition constant ($IC_{50}$ value) for the antagonist (as illustrated for Compound II in FIG. 2). Since Compound II was a partial agonist, it exhibited antagonist properties under this experimental regimen. The second protocol establishes the effect of increasing antagonist concentration on the agonist $EC_{50}$ value (as illustrated for Compound II in FIG. 3. At increasing concentrations, Compound II progressively shifted the dose-response curves of fluprostenol-induced [$^3$H]IPs production in A7r5 cells. Since the maximal effects of fluprostenol were unaltered, while its potency was reduced in the presence of the increasing concentrations of Compound II, the latter compound can be classified as a "competitive antagonist". Schild analysis of data from the second protocol yields quantitative antagonist potency data (as illustrated for Compound II in FIG. 4 and Table 1). FIG. 4 includes data from several experiments of the type described in FIG. 3. The transformed data in FIG. 4 indicate that the antagonist properties of Compound II were highly reproducible (n=9 experiments using 3T3 and A7r5 cells) and the potency of the compound determined by this method ($K_b$=132±22 nM) compared relatively well with that determined by the method shown in FIG. 2 ($K_i$=324±49 nM; n=3). Overall, the $K_i$ and $K_b$ values are synonymous and represent the antagonist potency of the antagonist at equilibrium. Two cell lines containing the FP receptor have been extensively characterized by this method, using known potent FP receptor agonists, as well as prostaglandins known to have some selectivity for other classes of prostaglandin receptors. These cell lines, available from the American Type Culture Collection, are the Swiss 3T3 embryonic albino mouse fibroblast line and the A7r5 rat thoracic aorta smooth muscle cell line.

TABLE 1

Potencies of Compounds Evaluated as Antagonists of the FP Receptor (A7r5 Cells)

| Compound | $K_b$, mol/L |
| --- | --- |
| Compound II | $1.32 \times 10^{-7}$ |
| PGF$_{2\alpha}$ dimethyl amide | Inactive |
| PGF$_{2\alpha}$ dimethyl amine | Inactive |
| Tolbutamide | Inactive |

TABLE 1-continued

Potencies of Compounds Evaluated as Antagonists of the FP Receptor (A7r5 Cells)

| Compound | $K_b$, mol/L |
| --- | --- |
| Glibenclamide | $1.6 \times 10^{-4}$ |
| Phloretin | $5.2 \times 10^{-6}$ |

The data in Table 1 indicate that Compound II has greater than 39-fold higher potency as an FP receptor antagonist than has phloretin; and that the other FP receptor antagonists are considerably less potent or inactive (i.e., tolbutamide, PGF$_{2\alpha}$ dimethyl amide and PGF$_{2\alpha}$ dimethyl amine). Also, Compound II, unlike phloretin, has relatively good selectivity for the FP prostaglandin receptor, compared to other classes of prostaglandin receptors.

EXAMPLE 2

Figure 2:
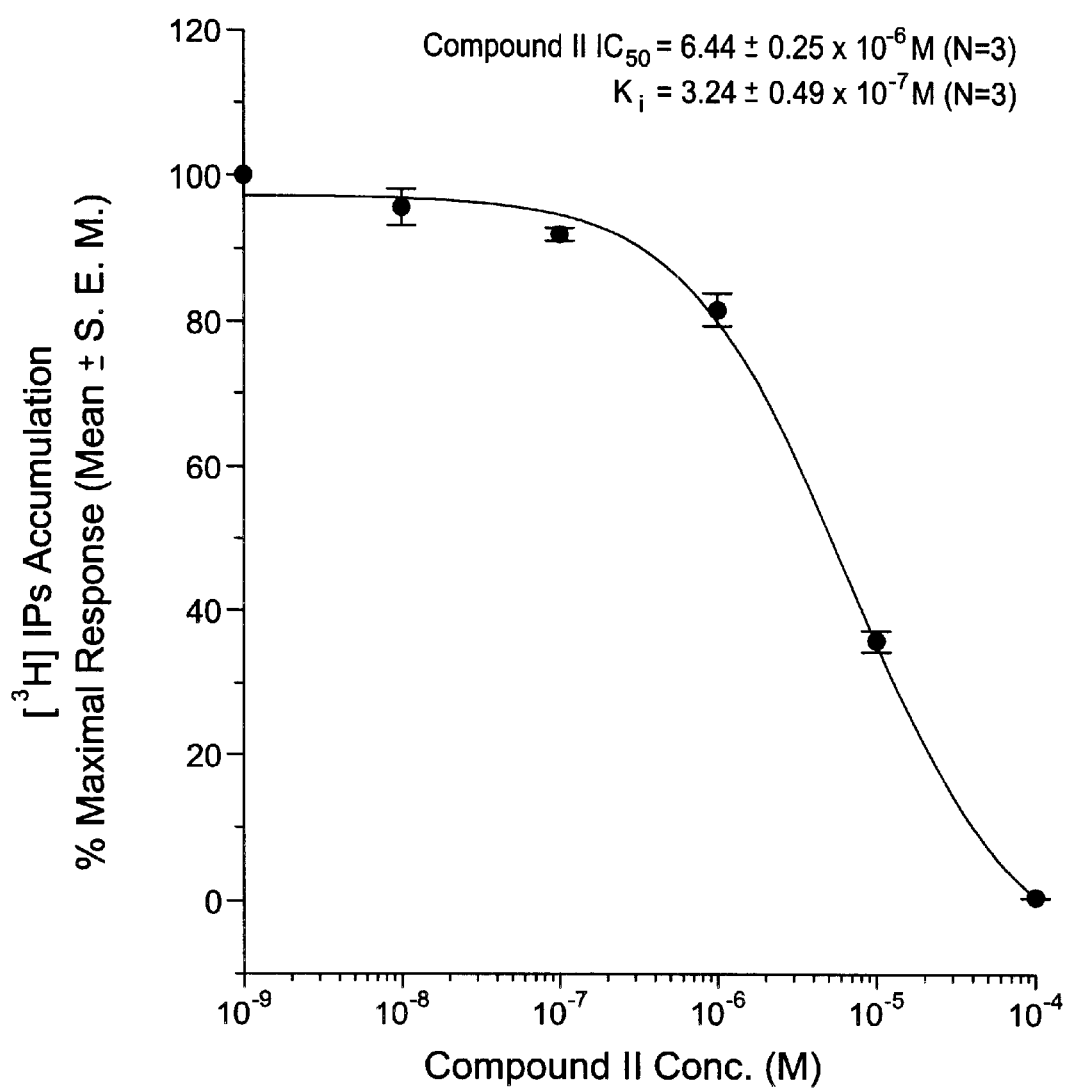
FIG. 2 is a graphical depiction of the concentration-dependent inhibition by Compound II of the fluprostenol-stimulated [$^3$H]IPs production in A7r5 cells.
Figure 3:
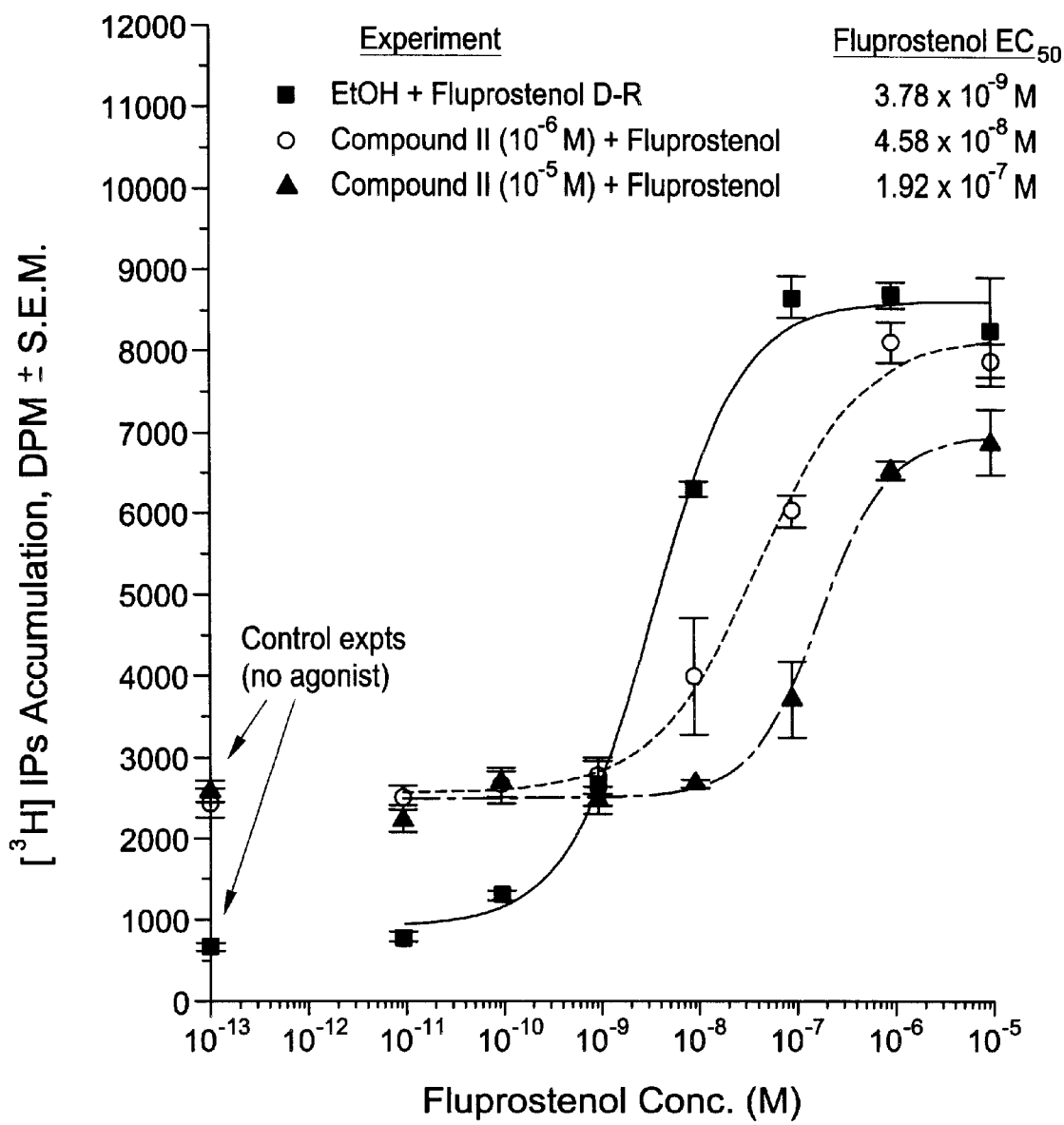
FIG. 3 is a graphical depiction of the antagonist properties of Compound II.
Figure 4:
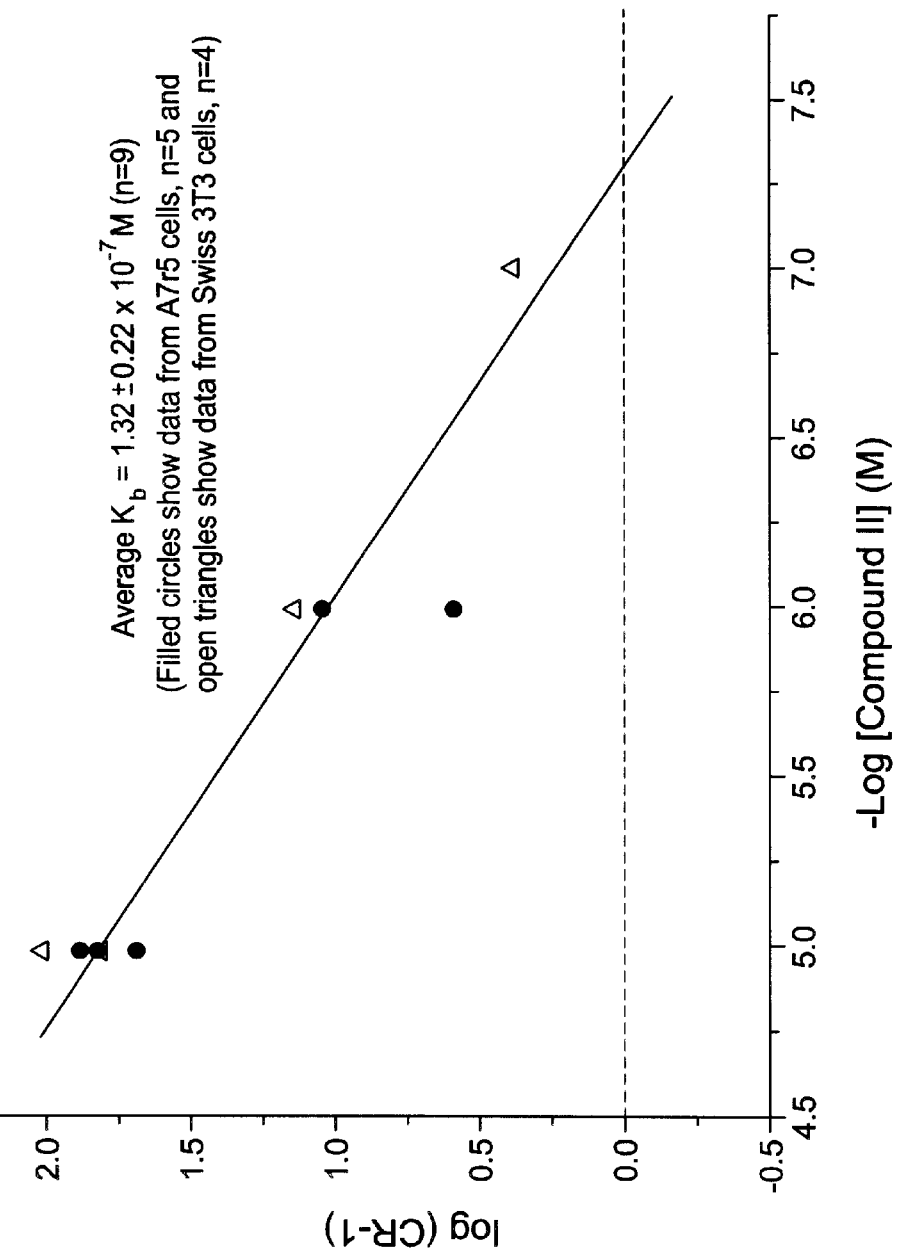
FIG. 4 is a graphical depiction of a Schild analysis for Compound II as an FP receptor antagonist tested in two cell types.

In order to determine if a test compound is an FP agonist, the type of experiment illustrated by FIGS. 2 and 3 is performed. Compound II (at 10 nM to 100 µM final concentrations) is added to [$^3$H]myo-inositol-labeled cells expressing an FP receptor 10–20 min prior to adding the test compound (at a fixed concentration which produces >50% of the maximal response) in the presence of 10 mM LiCl. The reaction is stopped and the [$^3$H]IPs produced in each well of the culture plate are determined by ion exchange chromatography as previously described in Example 3. The unknown agent's actions are found to be concentration-dependently inhibited by Compound II and the Schild-type experimental regimen (as exemplified in FIGS. 3 and 4) also yields the appropriate inhibition profile by Compound II. The unknown agent is therefore reliably classified as an FP agonist acting through an FP receptor-mediated signal transduction cascade.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of inhibiting an FP receptor-mediated response in a mammalian cell line or tissue where FP receptors are present and where the FP receptor-mediated response is selected from the group consisting of: inositol trisphosphate production, diacylglycerol production, mobilization of intracellular Ca$^{2+}$, activation of protein kinase C, tissue contraction, hormone release, fluid secretion, and initiation of an inflammatory response; comprising exposing the cell line or tissue to a receptor antagonizing effective amount of a compound of formula I:

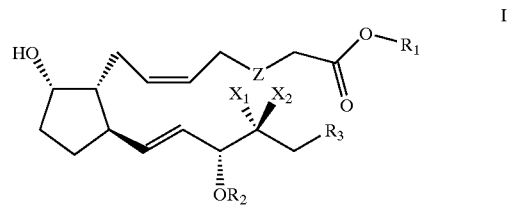

wherein:
R$_1$=H, C1–C5 alkyl or C3–C6 cycloalkyl, or a cationic salt moiety;

Z=$(CH_2)_n$, O, NH, or S; where n=1–3;

$R_2$=H, C1–C5 alkyl, or acyl;

one of $X_1$ or $X_2$=H, and the other halo; or $X_1$=$X_2$=halo; and $R_3$=$(CH_2)_2CH_3$, or phenyl, where the phenyl is optionally substituted with halogen, $CH_3$, $CF_3$, CN, $OCH_3$ or acetyl.

2. The method of claim 1, wherein the compound is of formula II:

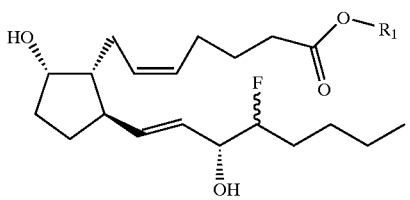

II wherein:

$R_1$=H or isopropyl;

and wherein the FP receptor-mediated response is selected from the group consisting: of inositol trisphosphate production, diacylglycerol production, mobilization of intracellular $Ca^{2+}$, and activation of protein kinase C.

3. A method of treating a mammal suffering from an FP receptor activation related disorder selected from the group consisting of: ocular hyperemia, cystoid macular edema, iris hyperpigmentation, iris melanogenesis, acute and chronic inflammation, benign prostatic hypertrophy, uterine cramps, irritable bowel disease, cardiac arrythmias, epilepsy, excessive bone deposition, and premature labor; comprising administering to said mammal a therapeutically effective amount of a compound of formula I:

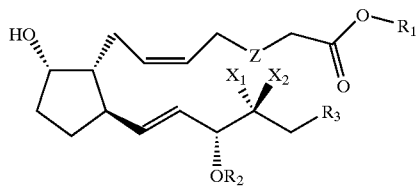

I wherein:

$R_1$=H, C1–C5 alkyl or C3–C6 cycloalkyl, or a cationic salt moiety;

Z=$(CH_2)_n$, O, NH, or S; where n=1–3;

$R_2$=H, C1–C5 alkyl, or acyl;

one of $X_1$ or $X_2$=H, and the other halo; or $X_1$=$X_2$=halo; and $R_3$=$(CH_2)_2CH_3$, or phenyl, where the phenyl is optionally substituted with halogen, $CH_3$, $CF_3$, CN, $OCH_3$ or acetyl.

4. The method of claim 3, wherein the FP receptor activation related disorder is selected from the group consisting of: ocular hyperemia, cystoid macular edema, iris hyperpigmentation, and iris melanogenesis.

5. The method of claim 4, wherein the compound is administered in a dosage range from about 0.00003% to about 1.0% (w/v %) in a biocompatible vehicle.

6. The method of claim 5, wherein the compound is of formula II:

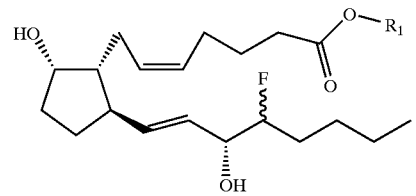

II wherein:

$R_1$=H or isopropyl.

7. A method of classifying a compound as an FP agonist, comprising:

exposing a mammalian cell line or tissue possessing FP receptors to the compound and taking a first measurement of an FP receptor mediated response of the cell line or tissue;

taking a second measurement of said FP receptor mediated response of the cell line or tissue having been exposed to an FP antagonist of formula I:

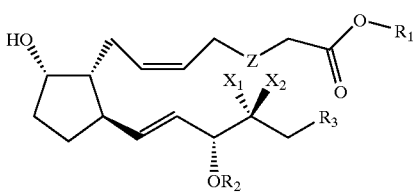

I $R_1$=H, C1–C5 alkyl or C3–C6 cycloalkyl, or a cationic salt moiety;

Z=$(CH_2)_n$, O, NH, or S; where n=1–3;

$R_2$=H, C1–C5 alkyl, or acyl;

one of $X_1$ or $X_2$=H, and the other halo; or $X_1$=$X_2$=halo; and $R_3$=$(CH_2)_2CH_3$, or phenyl, where the phenyl is optionally substituted with halogen, $CH_3$, $CF_3$, CN, $OCH_3$ or acetyl; and comparing the first and second measurements of the FP receptor mediated response of the cell line or tissue to determine the FP agonistic character of the compound.

8. The method of claim 7 wherein the measured FP receptor mediated response is selected from the group consisting of: inositol trisphosphate production, diacylglycerol production, mobilization of intracellular $Ca^{2+}$, and activation of protein kinase C.

9. The method of claim 8 wherein the FP antagonist is of formula II:

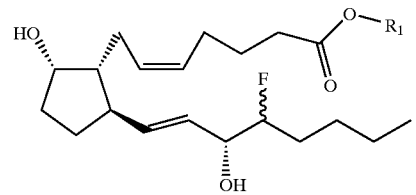

II wherein:

$R_1$=H or isopropyl.

* * * * *